United States Patent [19]

Hasselbring

[11] Patent Number: 4,982,043

[45] Date of Patent: Jan. 1, 1991

[54] ORGANIC SOLVENT TREATMENT FOR CATALYSTS AND OLEFIN DIMERIZATION PROCESSES THEREWITH

[75] Inventor: Lori C. Hasselbring, Bartlesville, Okla.

[73] Assignee: Phillips Petroleum Company, Bartlesville, Okla.

[21] Appl. No.: 325,637

[22] Filed: Mar. 20, 1989

[51] Int. Cl.$^5$ .................. B01J 21/18; B01J 38/50; C07C 2/24

[52] U.S. Cl. .................. 585/516; 502/29; 502/31; 502/33; 502/174

[58] Field of Search ............ 502/174, 31, 29, 33; 585/516

[56] References Cited

U.S. PATENT DOCUMENTS

| | | | |
|---|---|---|---|
| 2,930,765 | 3/1960 | Cooper et al. | 252/473 |
| 3,291,752 | 12/1966 | Keith et al. | 502/174 |
| 3,424,814 | 1/1969 | Keith et al. | 502/174 |
| 3,488,144 | 1/1970 | Sargent | 23/87 |
| 3,916,019 | 10/1975 | Closson et al. | 502/174 |
| 4,087,383 | 5/1978 | Gernand et al. | 252/463 |
| 4,520,126 | 5/1985 | Kawamoto et al. | 502/174 |
| 4,544,790 | 10/1985 | Drake | 585/516 |
| 4,609,637 | 9/1986 | Drake | 502/174 |

OTHER PUBLICATIONS

Dimerization of Propylene to 4-Methyl-1-Pentene with Catalysts Derived from Potassium, J. B. Wilkes, 1967, Proceedings of 7th World Petroleum Congress, vol. 5, pp. 299-309.

*Primary Examiner*—H. M. S. Sneed
*Assistant Examiner*—James Saba
*Attorney, Agent, or Firm*—Lynda S. Jolly

[57] ABSTRACT

Catalyst systems, methods to improve a catalyst system, and dimerization processes therewith are provided. Catalyst systems which comprise at least one elemental alkali metal supported on an alkali metal carbonate catalyst support, are contacted with a liquid organic solvent in order to improve the isomer ratio of the desired reaction product(s) to undesired product(s).

30 Claims, No Drawings

ORGANIC SOLVENT TREATMENT FOR CATALYSTS AND OLEFIN DIMERIZATION PROCESSES THEREWITH

BACKGROUND OF THE INVENTION

This invention relates to alkali metal carbonate supported alkali metal catalysts.

It is known in the art to employ alkali metal carbonate supported elemental alkali metal catalysts for such conversions as propylene dimerization. Several methods of preparing these types of catalysts are known in the art. The resultant catalyst systems although useful to dimerize olefins, do not always have a high isomer ratio of desired product(s) to undesired product(s). Thus, the dimerization process, because of a low isomer ratio, can be more time consuming and costly.

SUMMARY OF THE INVENTION

It is an object of this invention to provide an improved catalyst system for the dimerization of olefins.

It is another object of this invention to provide a method to treat a prepared alkali metal carbonate supported elemental alkali metal catalyst system.

It is yet another object of this invention to provide a process to improve the isomer ratio of the product(s) of an alkali metal carbonate supported elemental alkali metal catalyst system.

It is yet another object of this invention to provide an improved process for the dimerization of olefins.

In accordance with this invention, a dimerization catalyst comprising at least one elemental alkali metal on an alkali metal carbonate support is contacted, or treated, with at least one liquid organic solvent for a time sufficient to improve the isomer ratio of the desired product(s) to undesired product(s). The resultant treated catalyst system can have improved selectivity to the desired reaction product(s).

DESCRIPTION OF THE PREFERRED EMBODIMENTS

Supports

The catalyst support can be formed by any method known in the art. Thus, commercially available alkali metal carbonate in the form of powder, pellets, granules, or any other form can be treated directly with at least one elemental alkali metal and, optionally, one or more of the desired promoting materials as discussed more fully below. This form of support has the advantage of being most readily obtained with a minimum of handling.

In some circumstances, a large particle size and/or more rugged form of catalyst support is desired, such as, for example, where fixed bed reactions, especially large volume fixed bed reactions, are carried out. One particular technique for support preparation is to form a thick paste comprising alkali metal carbonate and water; alkali metal carbonate, water, and alcohol; or alkali metal carbonate, water, and water soluble ketone. The thick paste can be extruded, pelletized, pilled, or tabletted into appropriate sizes. The resultant material is then oven dried under conditions of time and temperature to insure that substantially all liquid is driven off. These types of supports will be referred to as "wet process" alkali metal carbonate supports.

Alcohols suitable for use in preparation of "wet process" catalyst supports are straight chain and branched aliphatic alcohols having from about 1 to about 7 carbon atoms. Water soluble ketones suitable for use in preparation of "wet process" catalyst supports are straight chain and branches water soluble ketones having from about 3 to about 7 carbon atoms.

In accordance with another technique for the support preparation alkali metal carbonate can be mixed with a non-acidic inorganic oxide and/or finely divided stainless steel. The mixture is heated to at least 950° C., then cooled, and finally, if desired, broken into pieces or fractionated to a desired particle size. Catalyst support prepared in this manner will be referred to as "melt process" alkali metal carbonate supports.

Suitable non-acidic inorganic oxides include, but are not limited to, alumina, such as alpha-alumina, silica, silica-alumina, magnesia-titania, thoria, magnesia, titania, zirconia, and mixtures of two or more thereof. Stainless steel as used herein is intended to cover broadly those alloys of iron which are relatively inert to the reaction conditions employed for olefin dimerization.

In accordance with another technique for the support preparation, an alkali metal carbonate is pelletized with at least one carbonaceous compound. The pelleted support, either as pellets or as smaller crushed particles, is then heated in an oxygen-containing atmosphere under conditions suitable to oxidize in the range of about 10 to about 90 weight percent of the carbonaceous compound. As a result of this partial oxidation of the pelleted support, the concentration of carbonaceous compound remaining on the surface of the support is substantially less than the concentration of carbonaceous compound remaining on the interior portions of the support. Catalyst support prepared in this manner will be referred to as "carbon containing" alkali metal carbonate support.

The term "carbonaceous compound" is intended to include various forms of the element carbon. Examples include, but are not limited to, carbon black, charcoal, coconut charcoal, amorphous graphite, and crystallite graphite.

Once the catalyst support is formed, it should be calcined in an oxygen-containing atmosphere at a temperature in the range of about 80° to about 350° C., preferably about 250° C., for a time of at least 2 hours. Times in excess of about 20 hours generally impart no additional beneficial affect. Thus, times in the range of about 2 to about 20 hours are useful. Upon completion of calcination, the catalyst support can be stored in a dry atmosphere. Preferably, the catalyst support is stored under a dry, oxygen-free atmosphere until needed for further treatment.

Catalysts and Promoters

Catalysts systems employed in the practice of this invention comprises one of the alkali metal carbonate supports described above, at least one elemental alkali metal catalyst, and optionally one or more of the following additional promoters:
  elemental copper,
  elemental cobalt,
  finely divided stainless steel,
  finely divided glass, and
  mixtures of two or more thereof.

It should be recognized, however, that the catalyst systems of the invention can contain additional components which do not adversely affect the catalyst performance, such as, for example, pigments, dyes, processing aids, inert fillers, binders and the like.

The alkali metals contemplated to be within the scope of the invention include lithium, sodium, potassium, rubidium and cesium. While the proportion of alkali metal combined with the alkali metal carbonate support can vary appreciably, generally at least about one weight percent of alkali metal based on the total weight of treated support will be employed. Generally, about 1 to about 20 weight percent alkali metal will be employed with about 2 to about 15 weight percent preferred. An alkali metal loading of about 3 to about 10 weight percent based on the total weight of treated support is most preferred for most efficient use of reagents, high catalyst activity and selectivity, and ease of catalyst preparation. Potassium is the preferred elemental alkali metal due to its ready availability as well as ease and safety in handling.

The portion of optional promoter on the alkali metal carbonate support can vary appreciably, but generally, at least one weight percent of the optional promoter based on the total weight of treated support will be employed. The following amounts are provided for additional guidance:

| | Loading, Weight Percent | | |
|---|---|---|---|
| Promoter | Broad | Intermediate | Preferred |
| Cu | 1–30 | 3–20 | 5–12 |
| Co | 1–50 | 3–25 | 5–15 |
| *SS | 1–80 | 3–60 | 5–50 |
| Glass | 1–50 | 2–25 | 3–15 |

*SS = Stainless Steel

The general procedure for preparation of the catalyst systems, after calcining the support, of the invention involves heating the alkali metal carbonate support to a temperature in the range of about 80° to about 350° C., preferably slightly above the melting point of the particular alkali metal used, cooling the particulate support and then contacting the particulate support with at least one elemental alkali metal in a dry, oxygen-free atmosphere, such as, for example $N_2$, Ar, or the like, at a temperature sufficient to cause the alkali metal to melt. The contacting, done in a dry, oxygen-free atmosphere, is preferably carried out with suitable mixing to ensure even distribution. Suitable temperatures for the contacting step will vary with the particular alkali metal employed. For example, with elemental potassium, temperatures in the range of about 80° to 110° C. are preferred, while with elemental sodium, temperatures in the range of about 100° to 140° C. are preferred.

While the alkali metal treated support is maintained at or above the melting point of the particular alkali metal used, in a dry, oxygen-free atmosphere, any desired promoter(s), such as for example, finely divided stainless steel or elemental copper, can be gradually added while the treated catalyst is continuously stirred. For example, with potassium, temperatures in the range of about 80° to about 110° C. are employed. The catalyst system is then ready to be charged to the reactor.

Optionally, the alkali metal carbonate support, once elemental alkali metal and any desired promoters have been deposited thereon, can be subjected to a subsequent heating step, in a dry, oxygen-free atmosphere, to ensure as uniform a distribution as possible of the various promoters on the surface of the alkali metal carbonate support. Thus, the finished catalyst system can be subjected to a temperature in the range of at least about 80° C. for a time in the range of about 0.1 to about 4 hours. A temperature in the range of about 100° to about 250° C. for a time in the range of about 0.5 to about 2 hours is presently preferred for the most uniform distribution.

Optionally, prior to charging the reactor, the catalyst system, defined as at least an alkali metal carbonate supported elemental alkali metal, can be mixed with an inert substance to dilute the catalyst system and decrease the rate of olefin dimerization. Any inert substance which has no catalytic activity in an olefin dimerization reaction can be used. One example of such an inert substance is glass beads.

As indicated by the variety of supports, alkali metal components, and promoters included within the scope of the invention, numerous catalyst combinations are possible. Any combination of the alkali metal and optional promoters disclosed can be supported on any alkali metal carbonate support disclosed. Some possible combinations are described in detail in the examples which follow. The combination of support, alkali metal and promoter(s) which one may choose to employ will depend on a variety of variables such as for example, reactor configuration, reaction temperature and pressure, olefin feed employed, rate of olefin feed, and conversions desired.

Organic Solvent Treatment

After the catalyst system has been prepared, it is then treated, before, during, or after use, or contacted, before, during, or after use, with at least one liquid organic solvent. As used in this disclosure, the terms "treating" and "contacting" are synonymous and the term "liquid" defines the state of the organic solvent after contacting the catalyst system, i.e., a gaseous organic solvent which contacts the catalyst system and condenses on the catalyst system to form a liquid organic solvent is within the scope of the term "liquid". While not wishing to be bound by theory, it is believed that the liquid organic solvent somehow interacts with the elemental alkali metal and/or dissolves the oligomerization reaction product adhered to the catalyst system. The resultant catalyst system can be more selective to the desired reaction product(s).

The liquid organic solvent which can be used in accordance with this invention is selected from the group consisting of saturated aliphatic hydrocarbon compounds, either normal, branched, and/or cyclic, having from about 1 to about 30 carbon atoms per molecule; olefinic aliphatic hydrocarbon compounds, either normal, branched, and/or cyclic, having from about 2 to about 30 atoms per molecule; aromatic hydrocarbon compounds, with or without aliphatic substitution, having from about 6 to about 30 carbon atoms per molecule; oxygen-containing organic compounds, such as, for example, alcohols, ketones, and/or ethers, having from about 1 to about 30 carbon atoms per molecule; and mixtures thereof. Preferably, the liquid organic solvent is selected from the group consisting of saturated aliphatic hydrocarbon compounds, either normal, branched, and/or cyclic, having from about 1 to about 10 carbon atoms per molecule; olefinic aliphatic hydrocarbon compounds, either normal, branched, and/or cyclic having from about 2 to about 10 carbon atoms per molecule; aromatic hydrocarbons, with or without aliphatic substitution, having from about 6 to about 15 carbon atoms per molecule; oxygen-containing organic compounds, such as, for example, alcohols, ketones, and/or ethers, having from about 1 to about 10 carbon atoms per molecule; and mixtures thereof. Most preferably, because of ease of use, reaction compatibility, availability, and economics, the liquid organic solvent is selected from the group consisting of saturated aliphatic hydrocarbon compounds, either normal or branched, having from about 2 to about 8 carbon atoms per molecule; olefinic aliphatic hydrocarbon compounds having from about 2 to about 8 carbon atoms per molecule; and mixtures thereof. Examples of some of the most preferred compounds include, but are not limited to, ethane, ethylene, propane, propylene, n-butane, 1-butene, 2-butene, isobutane, n-pentane, isopentane, 1-pentene, 2-pentene, n-hexane, 1-hexene, 2-hexene, 3-hexene, n-heptane, 4-methyl-1-pentene, and/or 4-methyl-2-pentene.

The time required to treat the catalyst system with the liquid organic solvent is any time sufficient to improve the selectivity to the desired product(s) and/or catalyst system activity. Minimal additional benefits can be obtained when the treatment time is excessive and too short of a contact time results in little or no catalyst system improvement. Usually, a time within the range of about 5 minutes to about 7 days is sufficient, preferably within the range of about 15 minutes to about 24 hours. Most preferably, the contact time is within the range of about 30 minutes to about 16 hours in order to maximize treatment time and beneficial effect to the catalyst.

The liquid organic solvent treatment of the catalyst system is done at a temperature sufficient to maintain the organic solvent in a liquid, or molten, state, yet not so high as to destroy or decompose the catalyst system and/or organic solvent. Suitable temperatures for the treating step will vary with the particular organic solvent employed. Temperatures within the range of about 0° C. to about 500° C. are usually employed; preferably the contacting temperature is within the range of about 0° C. to about 250° C. Most preferably, the treatment temperature is within the range of about 10° C. to about 180° C. because the dimerization reaction process usually occurs within this temperature range and, therefore, additional temperature regulation is not required.

The pressure during the liquid organic solvent treatment of the catalyst system can be any pressure that, when combined with the treatment temperature, is sufficient to maintain the organic solvent in a liquid, or molten, state, yet not so high, or low, as to destroy and/or decompose the catalyst system and/or solvent. Pressures within the range of about 0 pounds per square inch, gauge (psig) to about 5,000 psig are usually employed; preferably the treatment pressure is within the range of about 0 psig to about 2,500 psig. Most preferably, the treatment pressure is within about atmospheric pressure to about 2,000 psig because the dimerization reaction process usually occurs within this pressure range and, therefore, additional pressure regulation is not required.

The liquid organic solvent treatment can take place under any type of atmosphere. Preferably, the atmosphere is water-free and oxygen-free. Both water and oxygen can cause the catalyst system to decompose. A dry, inert atmosphere is preferred. Exemplary inert ambients include, but are not limited to, nitrogen, helium, and/or argon. For ease of use and availability, dry nitrogen, is the preferred ambient.

The volume of liquid organic solvent used to treat the catalyst system is any amount that can improve the catalyst system product isomer ratio. Usually a sufficient volume of liquid organic solvent is used to thoroughly immerse the catalyst system in solvent. Too little solvent can result in inefficient improvement and too much solvent can result in no additional benefit. The volume of solvent used can also depend on the type of contacting, i.e., batch or continuous, used.

The catalyst system can be contacted with the liquid organic solvent by batch and/or continuous mode, depending on the treatment facility. Any vessels and/or containers used during the treating process preferably are impervious to, and preferably do not react with, the catalyst system and/or organic solvent. The catalyst system is treated preferably after the catalyst system has been prepared in order to achieve maximum benefit. The treatment can be before, simultaneously (during), and/or after the dimerization process. For ease of treatment, the catalyst system and liquid organic solvent contacting can occur in the actual catalyst system containment, or reaction, vessel(s).

Reactants

Reactants applicable for use in the process of the invention are olefinic compounds which can (a) self-react, i.e., dimerize, to give useful products such as, for example, the self-reaction of propylene gives 4-methyl-1-pentene; and/or (b) olefinic compounds which can react with other olefinic compounds, i.e., co-dimerize, to give useful products such as, for example, co-dimerization of ethylene plus propylene gives 1-pentene, co-dimerization of ethylene and 1-butene gives 3-methyl-1-pentene and so forth. As used herein, the term "dimerization" is intended to include both self-reaction and "co-dimerization" as defined above.

Suitable dimerizable olefinic compounds are those compounds having from about 3 to about 30 carbon atoms and having at least one olefinic double bond and at least one allylic hydrogen atom, i.e., at least one hydrogen atom attached to a carbon atom adjacent to a double-bonded carbon atom. Exemplary compounds include, but are not limited to, acyclic and cyclic olefins such as for example propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, tetramethylethylene and the like; cyclopentene, cyclohexene, methylcyclopentene, methylcyclohexene, and the like and mixtures of any two or more thereof.

Suitable co-dimerizable olefinic compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of co-dimerizable olefins. Exemplary compounds in addition to those indicated above, include, but are not limited to ethylene, 3,3-dimethyl-1-butene, ditertiarybutyl ethylene and the like and mixtures of any two or more thereof.

The compounds indicated above as dimerizable olefinic compounds are capable of undergoing both self-reaction, i.e., dimerization, and cross-reaction, i.e., co-dimerization, with other members of the same group or with those compounds designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

Reaction Conditions

The dimerization reaction of the invention can be carried out using either batch or continuous types of operation, although the catalysts of the invention are particularly well suited for continuous, fixed bed operation. Suitable equipment such as, for example, autoclaves, tubular reactors and the like as are well known in the art can be employed. No special materials of construction are required so that steel, stainless steel, glass-lined reactors, or the like can be employed.

The reaction temperature can vary depending on the catalyst and feed(s) employed. Typically, a temperature range of about 50° to about 250° C. is suitable. Temperatures of about 80° to about 200° C. are preferred with a range of about 120° to about 170° C. most preferred because optimum reaction rates are obtained with minimum by-product formation.

The dimerization reaction can be carried out by contacting the dimerizable olefins with catalyst in the liquid phase, the gas phase, or the supercritical phase depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 100 to about 5,000 psig are employed, with pressure of about 1,000 to about 4,000 psig most preferred in order to achieve a good balance between reaction rate and minimize equipment and operating costs necessitated by very high reaction pressures.

If the reaction is carried out in the liquid phase, solvents or diluents for the reactants and/or catalyst can be used. Saturated aliphatic hydrocarbons, e.g., pentane, hexane, cyclohexane, dodecane; aromatic compounds, preferably those without an alpha-hydrogen (which would be capable of undergoing alkylation under the reaction conditions) such as benzene and chlorobenzene are suitable. If the reaction is carried out in the gaseous phase, diluents such as aliphatic hydrocarbons, for example methane, ethane and/or substantially inert gases, e.g., nitrogen, argon, can be present.

The contact time required for the dimerization reaction depends upon several factors such as, for example, the activity of the catalyst, temperature, pressure, structure of the reactants employed, level of conversion desired, and the like. The length of time during which the dimerizable olefinic compounds are contacted with catalyst can vary conveniently between about 0.1 seconds and about 24 hours although shorter and longer contact times can be employed. Preferably, times of about one minute to about 5 hours are employed. Where reaction is carried out in continuous fashion, it is convenient to express the reactant/catalyst contact time in terms of weight hourly space velocity (WHSV), i.e., the ratio of the weight of reactant which comes in contact with a given weight of catalyst per unit time. Thus, a WHSV of about 0.1 to about 10 will be employed. A WHSV of about 0.5 to about 5 is preferred, with about 1 to about 4 WHSV most preferred for optimum catalyst productivity.

Products

The olefinic products of the invention have established utility in a wide variety of applications such as for example as monomers for use in the preparation of homopolymers, copolymers, terpolymers, e.g., as the third component of ethylene-propylene terpolymers useful as synthetic elastomers, and the like.

A further understanding of the present invention and its advantages will be provided by reference to the following examples.

Examples

The catalyst support was prepared from commercially available, anhydrous potassium carbonate (JT Baker, ACS reagent grade), and deionized water. Water was mixed with potassium carbonate, particle size of equal to or less than about 0.42 mm (40 mesh) to form a thick paste. The thick paste was thoroughly mixed and extruded through a die plate with $\frac{1}{8}$" openings in a single screw, $2\frac{1}{4}$" Bonnot extruder. The extrudate was collected and allowed to break into pieces; each piece was from about $\frac{1}{4}$" to about $\frac{7}{8}$" long.

The extrudate was dried at about 150° C. in a vacuum oven for at least 2 hours. The dried extrudate was then calcined for about 3 hours in an oxygen-containing atmosphere at a temperature of at least about 250° C. and transferred to a dry, oxygen-free atmosphere. The resultant support was maintained at a temperature of about 80° to about 110° C., in an oxygen-free atmosphere, at which time about 4 to about 8 weight percent of elemental potassium and, optionally, about 5 weight percent of finely divided 316 stainless steel (about 325 mesh). At all times after calcination, the catalyst support and catalyst system were kept under a dry, inert atmosphere.

In each of the following Examples I–III, typically, the dimerization of propylene was carried out in a steam heated 316 stainless steel tubular reactor ($\frac{1}{2}$"×20"). The catalyst system was bounded at the outlet of the reactor by a small volume of glass beads. The catalyst system was combined with up to about 50 weight percent of an inert substance, i.e., no dimerization catalytic activity, to dilute the catalyst system and thus reduce and control the reaction rate. The contents of the tubular reactor were heated to the reaction temperature of about 160° C. at about 1500 psig and propylene was pumped into the reactor at a rate of about 120 mL/hr.

The dimerization of propylene in Example IV, typically, was carried out in a steam heated 316 stainless steel tubular reactor, wherein the diameter to length ratio was about 1:65. The catalyst system was bounded at the inlet and outlet of the reactor by a small volume of glass beads. The catalyst system was combined wtih up to about 50 weight percent of an inert substance, i.e., no dimerization catalytic activity, to dilute the catalyst system and thus reduce and control the reaction rate.

The contents of the tubular reactor were heated to the reaction temperature of about 150° C. at about 1400 psig and propylene was pumped into the reactor at a rate of about 65 lb/hr.

EXAMPLE I

Propylene was dimerized to 4-methyl-1-pentene (4MP1) in accordance with the above-identified procedure. An undesired isomer by-product of the reaction is 4-methyl-2-pentene (4MP2). However, one weight percent of n-heptane was added to the propylene feed in Run 102. The catalyst system in both Runs 101 and 102 was new, unused catalyst, prepared according to the previously-described procedure. The results are listed below in Table I.

TABLE I

| Run | n-Heptane Treatment | Propylene Conversion, % | 4MP1 Selectivity, % | 4MP1 4MP2 |
|---|---|---|---|---|
| 101 | none | 25 | 88 | 19 |
| 102 | in feed | 17 | 88 | 21 |

The data in Table I show that the addition of a liquid organic solvent, n-heptane, to the olefin feed improves the isomer ratio of 4MP1/4MP2. The percent selectivity to 4MP1 remains the same, while propylene conversion decreases.

EXAMPLE II

Example II is similar to Example I, except that the catalyst in all 3 runs had been on-stream to dimerize propylene for about 60 days. The catalyst in Run 202 was soaked for 15 minutes, at 98° C., atmospheric pressure, and under a dry nitrogen atmosphere, with a sufficient volume of n-heptane to thoroughly immerse and cover the catalyst. The catalyst in Run 203 was treated on-line, under the dimerization conditions given above, with one weight percent heptane in the propylene feed. The results are shown in Table II.

TABLE II

| Run | n-Heptane Treatment | Propylene Conversion, % | 4MP1 Selectivity, % | 4MP1 4MP2 |
|---|---|---|---|---|
| 201 | none | 16 | 86 | 14 |
| 202 | soak | 16* | 88 | 21 |
| 203 | in feed | 10 | 87 | 17 |

*value adjusted for small loss of catalyst system after soak procedure.

The data show that both the soak, or wash, treatment, as well as using a liquid organic solvent in the olefin feed, improve the isomer ratio for a used catalyst system. Furthermore, the soak treatment improves the catalyst system more than using only a liquid organic solvent in the olefin feed with little change in the conversion or selectivity.

EXAMPLE III

Catalyst systems in this Example were treated with different treating agents, for different lengths of time. Runs 301–306 were treated for about 16 hours, at a pressure within the range of 400–1000 psig, and a temperature within the range of 20° C. to 100° C.; the catalyst systems were completely immersed in the treating agent. Runs 307–309 were immersed in the treating agent for 15 minutes, at atmospheric pressure, under a dry nitrogen ambient, at the boiling point of the solvent (heptane is 98° C., toluene is 111° C.). Runs 310 and 311 were treated with a dry, inert gas for about 16 hours, at a pressure of 500 psig, and at a temperature within the range of 20° C. to 100° C. The inert gas used in Runs 310 and 311 was used to flush propylene from the reactor before treatment commenced.

TABLE III

| Run | Treating Agent | Propylene Conversion, % | | 4MP1 Selectivity, % | | 4MP1/4MP2 | | 4MP1/4MP2 % Change |
|---|---|---|---|---|---|---|---|---|
| | | Before | After | Before | After | Before | After | |
| 301 | Propylene | 23 | 28 | 88 | 89 | 19 | 29 | +53 |
| 302 | Propylene | 24 | 32 | 89 | 90 | 19 | 23 | +21 |
| 303 | Propylene | 17 | 18 | 89 | 90 | 25 | 33 | +32 |
| 304 | Propylene | 16 | 15 | 88 | 89 | 25 | 30 | +20 |
| 305 | Propylene | 16 | 19 | 90 | 90 | 30 | 28 | −7 |
| 306 | Propylene | 29 | 32 | 88 | 89 | 21 | 27 | +29 |
| 307* | Heptane | 16 | 16 | 86 | 88 | 14 | 21 | +50 |
| 308 | Toluene | 36 | 26 | 89 | 90 | 22 | 28 | +27 |
| 309 | Heptane | 14 | 14 | 89 | 88 | 28 | 30 | +7 |
| 310 | Nitrogen | 13 | 14 | 89 | 89 | 33 | 30 | −9 |
| 311 | Helium | 8 | 8 | 87 | 86 | 18 | 17 | −6 |

*Spent catalyst, after 60 days on-line of propylene dimerization.
All other Runs were with new, unused catalyst.

The data in Table III show that, while propylene conversion (after the induction period) and 4MP1 selectivity remain fairly constant, treatment with a liquid organic solvent improves the 4MP1/4MP2 isomer ratio. Run 305 is an unexplainable anomaly wherein the isomer ratio decreased; one possibility is that water and/or oxygen got into the treatment vessel. The data of Runs 310 and 311 also show that treatment with inorganic compounds can even negatively affect the isomer ratio.

EXAMPLE IV

The catalyst used in Example IV was used over approximately a 3-month period and was soaked about once per week in propylene. The catalyst system and propylene contacting was 400 psig. The temperature during treatment initially was about 100° C. and then allowed to cool to about 20° C. (room temperature). Table IV shows the resultant data.

TABLE IV

| Day | 4MP1/4MP2 | Day | 4MP1/4MP2 |
|---|---|---|---|
| 1* | 38 | 48* | 18 |
| 2 | 26 | 49 | 21 |
| 3 | 24 | 50 | 18 |
| 7* | 37 | 51 | 18 |
| 8 | 32 | 52 | 18 |
| 9 | 29 | 55* | 19 |
| 10 | 26 | 56 | 17 |
| 13* | 30 | 57 | 17 |
| 14 | 27 | 58 | 17 |
| 15 | 25 | 61* | 18 |
| 16 | 24 | 62 | 16 |
| 17 | 23 | 63 | 15 |
| 20* | 24 | 64 | 16 |

TABLE IV-continued

| Day | 4MP1/4MP2 | Day | 4MP1/4MP2 |
|---|---|---|---|
| 21 | 27 | 68* | 18 |
| 22 | 24 | 69 | 16 |
| 23 | 22 | 70 | 16 |
| 24 | 23 | 71 | 16 |
| 27* | 24 | 72 | 15 |
| 28 | 22 | 75* | 17 |
| 29 | 24 | 76 | 15 |
| 30 | 22 | 77 | 15 |
| 34* | 22 | 78 | 15 |
| 35 | 22 | 82* | 19 |
| 36 | 21 | 83 | 15 |
| 37 | 20 | 84 | 15 |
| 38 | 18 | 85 | 14 |
| 41* | 23 | 86 | 15 |
| 42 | 20 | 89* | 17 |
| 43 | 19 | 90 | 17 |
| 44 | 24 | 91 | 16 |
| 45 | 23 | 92 | 17 |

*Propylene treatment was on the preceding day(s); dimerization was re-started on these days.

The propylene conversion and 4MP1 selectivity was fairly constant during this time period. However, the above-given data show that the isomer ratio improved each time propylene treatment was administered to the catalyst system.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A process for preparing a treated catalyst system which improves the isomer ratio of the desired product(s) to undesired products and catalyst activity, wherein said process comprises contacting before or after use, a catalyst system which comprises at least one elemental alkali metal supported on an alkali metal carbonate with a liquid organic solvent, at a temperature within a range of about 0° to about 500° C.; a pressure within the range of about 0 to about 5000 psig; under a dry, inert atmosphere; and for a time within the range of about 5 minutes to about 7 days.

2. A process according to claim 1 wherein said solvent is selected from the group consisting of saturated aliphatic hydrocarbon compounds having from about 1 to about 30 carbon atoms per molecule; olefinic aliphatic hydrocarbon compounds having from about 2 to about 30 carbon atoms per molecule; aromatic compounds having from about 6 to about 30 carbon atoms per molecule; oxygen-containing organic compounds having from about 1 to about 30 carbon atoms per molecule; and mixtures thereof.

3. A process according to claim 2 wherein solvent is selected from the group consisting of saturated aliphatic hydrocarbon compounds having from about 2 to about 8 carbon atoms per molecule; olefinic aliphatic hydrocarbon compounds having from about 2 to about 8 carbon atoms per molecule; aromatic hydrocarbon compounds having from about 6 to about 12 carbon atoms per molecule; and oxygen-containing organic compounds having from about 1 to about 10 carbon atoms per molecule; and mixtures thereof.

4. A process according to claim 2 wherein said solvent is selected from the group consisting of propylene, n-hexene, n-heptane 4-methyl-1-pentene, 4-methyl-2-pentene, and mixtures thereof.

5. A process according to claim 1 wherein said elemental alkali metal is selected from the group consisting of lithium, sodium, potassium, rubidium, and cesium.

6. A process according to claim 1 wherein said alkali metal carbonate is selected from the group consisting of sodium carbonate, potassium carbonate, and mixtures thereof.

7. A process according to claim 1 wherein said catalyst system comprises elemental potassium supported on potassium carbonate.

8. A process according to claim 1 wherein said contacting occurs before the catalyst has been used to dimerize any olefin.

9. A process according to claim 1 wherein said contacting occurs after the catalyst has been used to dimerize olefins.

10. A process for preparing a treated catalyst system which improves the isomer ratio of the desired product(s) to undesired, wherein said process comprises contacting before or after use, a catalyst system which comprises elemental potassium supported on potassium carbonate with a liquid organic solvent selected from the group consisting of propylene, n-hexene, n-heptane, 4-methyl-1-pentene, 4-methyl-2-pentene, and mixtures thereof, at a temperature within a range of about 0° to about 500° C.; a pressure within the range of about 0 to about 5000 psig; under a dry, inert atmosphere; and for a time within the range of about 5 minutes to about 7 days.

11. A catalyst system produced according to the process of claim 1.

12. A catalyst system produced according to the process of claim 10.

13. A dimerization process comprising contacting olefins under dimerization conditions with a catalyst system which improves the isomer ratio of the desired product(s) to undesired products and catalyst activity, wherein said catalyst system is prepared by contacting, before or after use, at least one elemental alkali metal supported on an alkali metal carbonate with a liquid organic solvent, at a temperature within a range of about 0° to about 500° C.; a pressure within the range of about 0 to about 5000 psig; under a dry, inert atmosphere; and for a time within the range of about 5 minutes to about 7 days.

14. A process according to claim 13 wherein said olefin is propylene and wherein said propylene is converted to 4-methyl-1-pentene.

15. A process according to claim 13 wherein said solvent is selected from the group consisting of saturated aliphatic hydrocarbon compounds having from about 1 to about 30 carbon atoms per molecule; olefinic aliphatic hydrocarbon compounds having from about 2 to about 30 carbon atoms per molecule; aromatic compounds having from about 6 to about 30 carbon atoms per molecule; oxygen-containing organic compounds having from about 1 to about 30 carbon atoms per molecule; and mixtures thereof.

16. A process according to claim 15 wherein solvent is selected from the group consisting of saturated aliphatic hydrocarbon compounds having from about 2 to about 8 carbon atoms per molecule; olefinic aliphatic hydrocarbon compounds having from about 2 to about 8 carbon atoms per molecule; aromatic hydrocarbon compounds having from about 6 to about 12 carbon atoms per molecule; and oxygen-containing organic compounds having from about 1 to about 10 carbon atoms per molecule; and mixtures thereof.

17. A process according to claim 16 wherein said solvent is selected from the group consisting of propylene, n-hexene, n-heptane, 4-methyl-1-pentene, 4-methyl-2-pentene, and mixtures thereof.

18. A process according to claim 13 wherein said time of contact is within the range from about 15 minutes to about 24 hours.

19. A process according to claim 13 wherein said elemental alkali metal is selected from the group consisting of lithium, sodium, potassium, rubidium, and cesium.

20. A process according to claim 13 wherein said alkali metal carbonate is selected from the group consisting of sodium carbonate, potassium carbonate, and mixtures thereof.

21. A process according to claim 13 wherein said catalyst system comprises elemental potassium supported on potassium carbonate.

22. A process according to claim 13 wherein said contacting occurs before the catalyst has been used to dimerize olefin.

23. A process according to claim 13 wherein said contacting occurs after the catalyst has been used to dimerize olefins.

24. A process according to claim 13 wherein said olefin contacting is carried out at a temperature in the range of about 80° to about 200° C., a pressure in the range of about 1000 to about 4000 psig, and a weight hourly space velocity in the range of about 0.1 to about 10.

25. A process for the production of 4-methyl-1-pentene comprising contacting propylene under dimerization conditions with a catalyst system which improves the isomer ratio of the desired product(s) to undesired products and catalyst activity, wherein said catalyst system is prepared by contacting, before or after use, elemental potassium supported on potassium carbonate with a liquid organic solvent selected from the group consisting of propylene, n-hexene, n-heptane, 4-methyl-1-pentene, 4-methyl-2-pentene, and mixtures thereof, at a temperature within a range of about 0° to about 500° C.; a pressure within the range of about 0 to about 5000 psig; under a dry, inert atmosphere; and for a time within the range of about 5 minutes to about 7 days.

26. A process according to claim 25 wherein said propylene contacting is carried out at a temperature in the range of about 80° to about 200° C., a pressure in the range of about 1000 to about 4000 psig, and a weight hourly space velocity in the range of about 0.1 to about 10.

27. A process for preparing a treated catalyst system which improves the isomer ratio of the desired product(s) to undesired products and catalyst activity, wherein said process comprises contacting a catalyst system which comprises at least one elemental alkali metal supported on an alkali metal carbonate with a liquid organic solvent, at a temperature within a range of about 0° to about 500° C.; a pressure within the range of about 0 to about 5000 psig; under a dry, inert atmosphere; and for a time within the range of about 5 minutes to about 7 days, and wherein said contacting occurs before the catalyst system has been used to dimerize olefins.

28. A process for preparing a treated catalyst system which improves the isomer ratio of the desired product(s) to undesired products and catalyst activity, wherein said process comprises contacting a catalyst system which comprises at least one elemental alkali metal supported on an alkali metal carbonate with a liquid organic solvent, at a temperature within a range of about 0° to about 500° C.; a pressure within the range of about 0 to about 5000 psig; under a dry, inert atmosphere; and for a time within the range of about 5 minutes to about 7 days, and wherein said contacting occurs after the catalyst system has been used to dimerize olefins.

29. A dimerization process comprising contacting olefins under dimerization conditions with a catalyst system which improves the isomer ratio of the desired product(s) to undesired products and catalyst activity, wherein said catalyst system is prepared by contacting, before use, at least one elemental alkali metal supported on an alkali metal carbonate with a liquid organic solvent, at a temperature within a range of about 0° to about 500° C.; a pressure within the range of about 0 to about 5000 psig; under a dry, inert atmosphere; and for a time within the range of about 5 minutes to about 7 days.

30. A dimerization process comprising contacting olefins under dimerization conditions with a catalyst system which improves the isomer ratio of the desired product(s) to undesired products and catalyst activity, wherein said catalyst system is prepared by contacting, after use, at least one elemental alkali metal supported on an alkali metal carbonate with a liquid organic solvent, at a temperature within a range of about 0° to about 500° C.; a pressure within the range of about 0 to about 5000 psig; under a dry, inert atmosphere; and for a time within the range of about 5 minutes to about 7 days.

* * * * *